United States Patent
Daniewski et al.

(10) Patent No.: US 6,353,123 B1
(45) Date of Patent: Mar. 5, 2002

(54) PROCESS AND INTERMEDIATES USEFUL TO PRODUCE VITAMIN D ANALOGS

(75) Inventors: Andrzej Robert Daniewski, Bloomfield; Marek Michal Kabat; Masami Okabe, both of Nutley; Roumen Nikolaev Radinov, West Caldwell, all of NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/835,593

(22) Filed: Apr. 16, 2001

Related U.S. Application Data

(62) Division of application No. 09/633,672, filed on Aug. 7, 2000.
(60) Provisional application No. 60/150,378, filed on Aug. 23, 1999.

(51) Int. Cl.$^7$ ............................................. C07D 303/00
(52) U.S. Cl. ...................................................... 549/546
(58) Field of Search .......................................... 549/546

(56) References Cited

PUBLICATIONS

Suzuki, M.; Oda, Y;; Noyori, R., J. Amer. Chem. Soc., 101, pp. 1623–1625 (1979).
Shiuey, S.–J.; Kulesha, I.; Baggiolini,E.G.; Uskokovic, M.; J. Org. Chem., 55, pp. 243–247 (1990).
Baggiolini et al, J. Org. Chem., 51, pp. 3098–3108, 1986.

*Primary Examiner*—Ba K. Trinh
(74) *Attorney, Agent, or Firm*—George W. Johnston; John P. Parise

(57) ABSTRACT

A stereospecific method for accomplishing the below reaction:

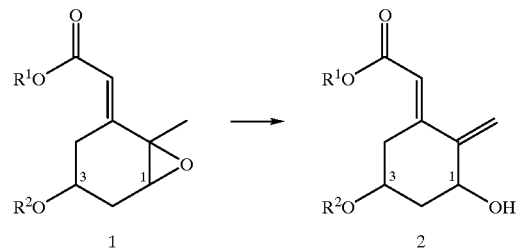

results in the compound of formula 2 having the same stereochemistry at both carbon 1 and carbon 3 as that in the compound of formula 1. Thus, if carbon 3 is in the R-configuration in the compound of formula 1, then carbon 3 will be in the R-configuration in the compound of resulting formula 2. In the above process, $R^1$ is $C_1$–$C_6$ alkyl that can be straight-chain or branched. The process functions using a fluorinated alcohol having a $pK_a$ less than about 9, in the presence of a palladium catalyst. The compounds of formula 1, as well as novel intermediates in this process, are useful in manufacturing vitamin D analogs.

16 Claims, No Drawings

PROCESS AND INTERMEDIATES USEFUL TO PRODUCE VITAMIN D ANALOGS

CROSS REFERENCE TO RELATED APPLICATION

This is a divisional of copending patent application Ser. No. 09/633,672, filed Aug. 7, 2000, which claims the benefit of U.S. Provisional Application No. 60/150,378 filed Aug. 23, 1999.

BACKGROUND

1. Field

The invention relates to a process useful to produce vitamin D analogs, such as calcitriol, sold under the brand name Rocaltrol®.

2. Description

Processes for manufacturing vitamin D analogs typically require multiple steps and chromatographic purification. See, Norman, A. W.; Okamura, W. H. PCT Int. Appl. WO 9916452 A1 990408; Chem Abstr. 130:282223. Batcho, A. D.; Bryce, G. F.; Hennessy, B. M.; Iacobelli, J. A.; Uskokovic, M. R. Eur. Pat. Appl. EP 808833, 1997; Chem. Abstr. 128:48406. Nestor, J. J.; Manchand, P. S.; Uskokovic, M. R. Vickery, B. H. U.S. Pat. No. 5,872,113, 1997; Chem. Abstr. 130:168545. The present invention seeks to provide an efficient synthesis of the A-ring portion of such vitamin D analogs.

SUMMARY OF THE INVENTION

The subject invention provides a method of stereospecifically producing a compound of formula:

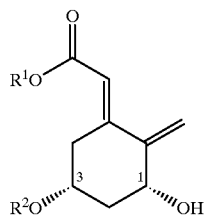

2AA or its enantiomer

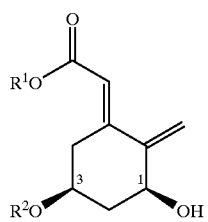

2AA* wherein $R^1$ is $C_1$–$C_6$ alkyl and $R^2$ is a hydroxy protective group, which comprises reacting a compound of formula:

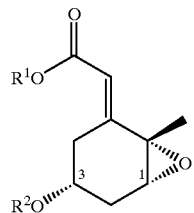

1AA or its enantiomer, respectively,

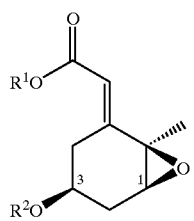

1AA* wherein $R^1$ and $R^2$ are as above and the stereochemistry of both the compound of formula 1AA and the compound of formula 2AA is the same at carbons 1 and 3, respectively, and the stereochemistry of both the compound of formula 1AA* and the compound of formula 2AA* is the same at carbons 1 and 3, respectively, with a fluorinated alcohol having a $pK_a$ lower than about 9, in the presence of a palladium catalyst to yield the compound of formula 2AA or 2AA*, respectively.

The palladium catalyst is typically a palladium-phosphine catalyst, such as palladium-triarylphosphine. Preferred palladium-triarylphosphine catalysts are selected from the group consisting of palladium-triphenylphosphine, palladiumtris(2-methoxyphenyl)phosphine, palladium-tris(3-methoxyphenyl)phosphine, palladium-tris(4-methoxyphenyl)phosphine, palladium-tris(o-tolyl)phosphine, palladium-tris(m-tolyl)phosphine, palladium-tris(p-tolyl)phosphine, palladium-tris(4-fluorophenyl)phosphine, palladium-tris(p-trifluoromethylphenyl)phosphine, and palladium-tris(2-furyl)phosphine. Another palladium catalyst is palladium-1,2-bis(diphenylphosphino)ethane.

The fluorinated alcohol is favorably selected from the group consisting of:

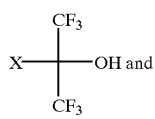

15

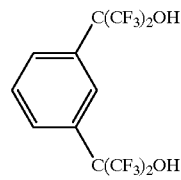

16 wherein X is phenyl or $CF_3$. Of these fluorinated alcohols, the compounds

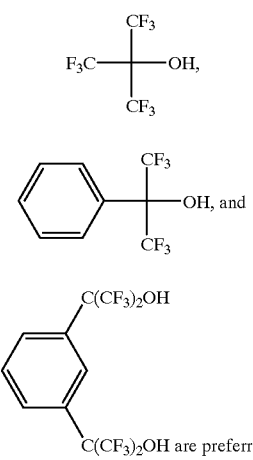

Novel intermediates provided by the subject invention include a compound having the structure:

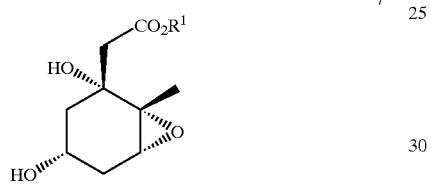

wherein $R^1$ is $C_1$–$C_6$ alkyl; or preferably a compound of the structure:

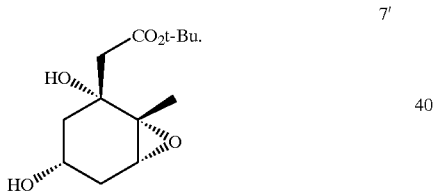

These intermediates and the compounds that follow, as well as their enantiomers, form a portion of the subject application.

Another novel intermediate is a compound having the structure:

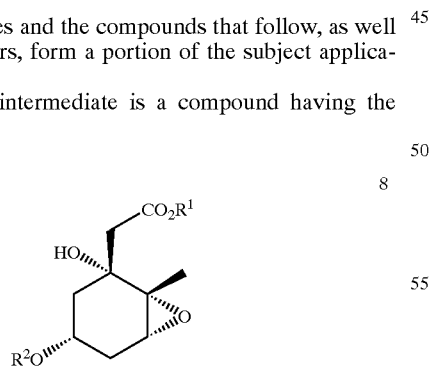

wherein $R^1$ is $C_1$–$C_6$ alkyl and $R^2$ is a hydroxy protective group selected from the group consisting of trimethylsilyl, triethylsilyl, tripropylsilyl, triisopropylsilyl, t-butyidimethylsilyl ("TBS"), dimethylthexylsilyl, triphenylsilyl, and t-butyidiphenylsilyl. Preferably, this compound has the structure:

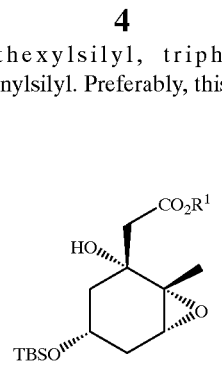

wherein $R^1$ is $C_1$–$C_6$ alkyl, or the structure:

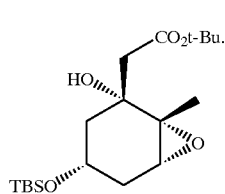

wherein $R^2$ is a hydroxy protective group selected from the group consisting of trimethylsilyl, triethylsilyl, tripropylsilyl, triisopropylsilyl, t-butyldimethylsilyl, dimethylthexylsilyl, triphenylsilyl, and t-butyldiphenylsilyl; or a compound of the structure:

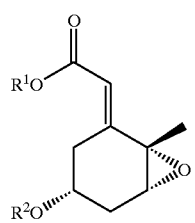

Yet another novel intermediate is the compound having the structure:

wherein $R^1$ is $C_1$–$C_6$ alkyl and $R^2$ is a hydroxy protective group selected from the group consisting of trimethylsilyl, triethylsilyl, tripropylsilyl, triisopropylsilyl, t-butyldimethylsilyl, dimethylthexylsilyl, triphenylsilyl, and t-butyldiphenylsilyl; or the compound having the structure:

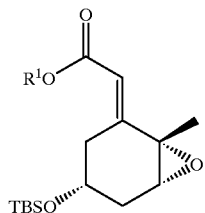

1A″ wherein R¹ is C₁–C₆ alkyl; or the compound having the structure:

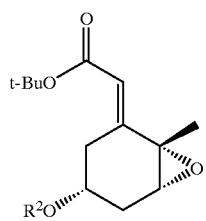

1A‴ wherein R² is a hydroxy protective group selected from the group consisting of trimethylsilyl, triethylsilyl, tripropylsilyl, triisopropylsilyl, t-butyldimethylsilyl, dimethylthexylsilyi, triphenylsilyl, and t-butyldiphenylsilyl; or the compound having the structure:

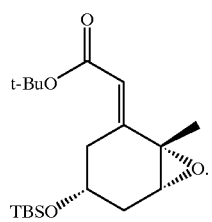

1A′

Other novel intermediates include a compound having the structure:

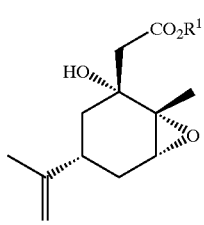

4 wherein R¹ is C₁–C₆ alkyl; or the compound having the structure:

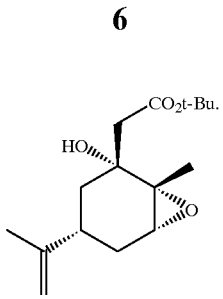

4′

The novel intermediate having the structure:

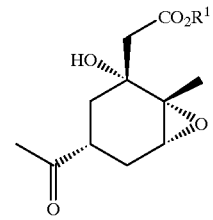

5 wherein R¹ is C₁–C₆ alkyl; and the compound having the structure:

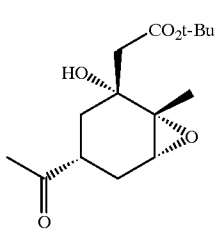

5′ are also provided. Other intermediates include the compound having the structure:

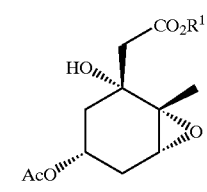

6 wherein R¹ is C₁–C₆ alkyl; and the compound having the structure:

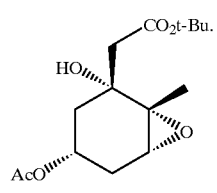

6′

DETAILED DESCRIPTION OF THE PREFERRED EMBODIMENTS

The subject invention will now be described in terms of its preferred embodiments. These embodiments are set forth to aid in understanding the invention but are not to be construed as limiting.

The subject invention is concerned generally with a stereospecific and regioselective process for converting compounds of formula 1 to compounds of formula 2. However, as explained below, there are certain differences between the processes involving compounds of formula 1 wherein the substituents at the 1 and 3 carbons are attached cis-, i.e. on the same side of the plane of the six-membered ring, and compounds of formula 1 wherein the substituents at the 1 and 3 carbons are attached trans-, i.e. on opposite sides of the plane of the six-membered ring.

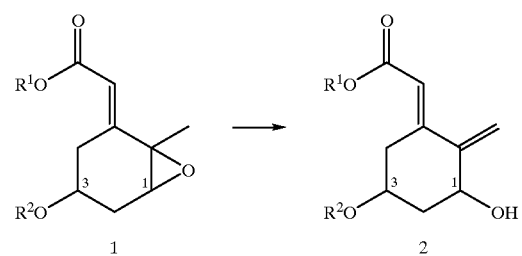

The process results in the compound of formula 2 having the same relative and absolute stereochemistry at both carbon 1 and carbon 3 as that in the compound of formula 1. Thus, if carbon 1 is in the R-configuration in the compound of formula 1, then carbon 1 will be in the R-configuration in the compound of resulting formula 2. In the above process, $R^1$ is $C_1$–$C_6$ alkyl that can be straight-chain or branched. For example, methyl, ethyl, propyl, isopropyl, butyl (primary, secondary or tertiary), pentyl (primary, secondary or tertiary), or hexyl (primary, secondary or tertiary). $R^2$ is a hydroxy protective group. The choice of protective group is readily determinable by the skilled artisan. However, a silyl protective group, such as tert-butyldimethylsilyl ("TBS") is preferred.

The bonds forming the epoxide ring may be above the plane or below the plane of the molecule. When the epoxide ring is below the plane, the adjacent methyl group is above the plane. Likewise, when the epoxide ring is above the plane, the adjacent methyl is below the plane.

For example, when the substituents at carbons 1 and 3 are cis, the following situations can occur:

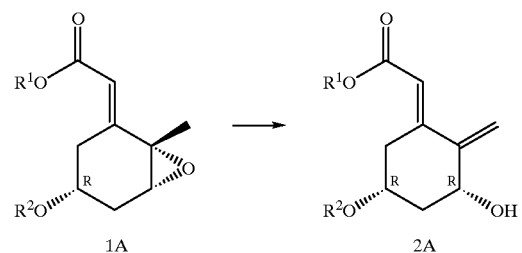

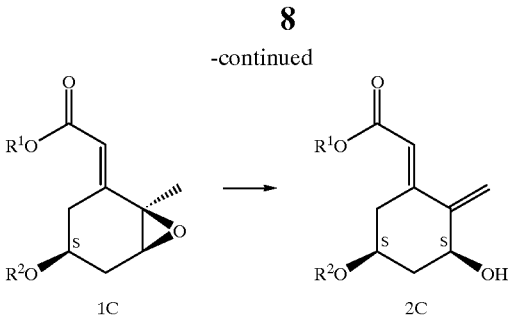

When the substituents at carbons 1 and 3 are trans, the following situations can occur:

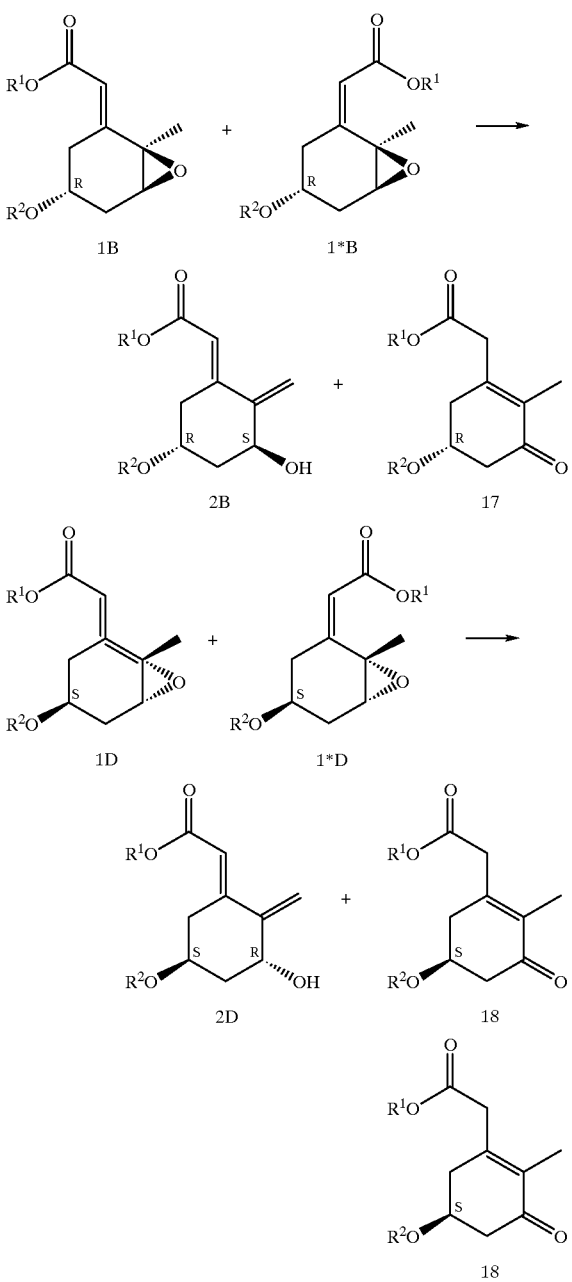

Compounds of formula 2A–D are useful for the preparation of Vitamin D analogs, for example, for compound 2A, see: Shiuey, S. J.; Kulesha, I.; Baggiolini, E. G.; Uskokovic, M. R. *J. Org. Chem.* 1990, 55, 243; for compound 2B, see: Nagasawa, K.; Zako, Y.; Ishihara, H.; Shimizu, I. *Tetrahedron Lett* 1991, 32, 4937. Nagasawa, K.; Zako, Y.; Ishihara, H.; Shimizu, I. *J. Org. Chem.* 1993, 58, 2523; for compound 2C, see: Hatakeyama, S.; Iwabuchi, Y. PCT Int. Appl. WO 9915499 A1 990401; *Chem. Abstr.* 130:252533; and. for compound 2D, see: Shimizu, N. Jpn. Kokai Tokkyo Koho JP 04305553 A2 921028; *Chem. Abstr* 118:191249. Shimizu, N. Jpn. Kokai Tokkyo Koho JP 04305548 A2 921028; *Chem. Abstr.* 118:212477. Minojima, T.; Tomimori, K.; Kato, Y. Jpn. Kokai Tokkyo Koho JP 02286647 A2 901126; *Chem. Abstr.* 114:184872.

Compounds of formula 1A and 1C are enantiomers, and can be prepared from known compounds. For example, the starting material may be (+)-Carvone for the preparation of 1A, and the starting material may be (−)-Carvone for the preparation of 1C [Liu, H. J.; Zhu, B. Y. *Can. J. Chem.* 1991, 69, 2008]. The compound of formula 3 or its enantiomer may be obtained by reacting (+)-carvone or (−)-carvone, respectively, with an acetic acid ester, such as methylacetate, ethylacetate, propylacetate, isopropylacetate, t-butyl, isobutyl, or sec-butyl acetate, pentyl (primary, seconadry or tertiary) acetate, or hexyl (primary, seconadry or tertiary) acetate, according to procedures set forth in the above publication. A skilled chemist having read the present specification would know how to produce a given enantiomer by choosing the corresponding enantiomeric starting material.

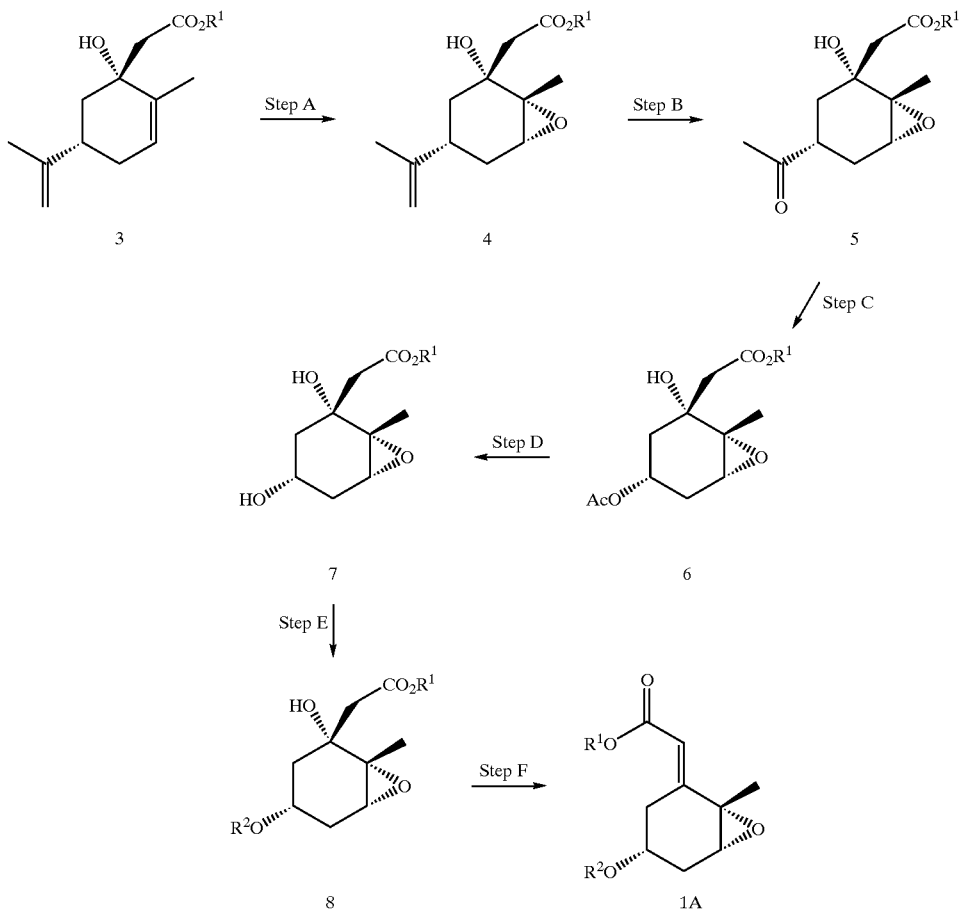

In the compounds of the above scheme, $R^1$ is $C_1$–$C_6$ alkyl that can be straight-chain or branched. For example, methyl, ethyl, propyl, isopropyl, butyl (primary, secondary or tertiary), pentyl (primary, secondary or tertiary), or hexyl (primary, secondary or tertiary). $R^2$ is a hydroxy protective group, for example a silyl protective group. The choice of hydroxy protective group is readily apparent to the skilled artisan, see for example T. W. Greene, P. G. M. Wuts, Protective Groups in Organic Synthesis, $2^{nd}$ Ed., John Wiley & Sons, 1991. Acceptable hydroxy protective groups for use in connection with the subject invention include silyl ethers such as trimethylsilyl, triethylsilyl, tripropylsilyl, triisopropylsilyl, t-butyldimethylsilyl, dimethylthexylsilyl, triphenylsilyl, and t-butyldiphenylsilyl.

Step A of the above process is the highly regio- and stereoselective epoxidation of the known [Liu, H. J.; Zhu, B. Y. *Can. J. Chem.* 1991, 69, 2008] allyl alcohol of formula 3 catalyzed by vanadyl acetylacetonate to obtain the epoxide of formula 4. The side chain double bond is then ozonized to give the ketone of formula 5. A Baeyer-Villiger oxidation of the ketone of formula 5, followed by hydrolysis of the resulting acetate 6 gave alcohol 7. Selective silylation of the secondary alcohol and dehydration of the tertiary alcohol gave unsaturated ester of formula 1A in the (E) configuration.

Step A

The allyl alcohol of formula 3 can be epoxidized in methylene chloride using a catalytic amount of vanadyl acetylacetonate and a nonane solution of tert-butyl hydroperoxide in the presence of molecular sieves. Alternatively, the reaction can be carried out in refluxing cyclohexane with constant removal of water by a Dean-Stark condenser, using 1.5 mol % of the vanadium complex and about 1.2 equiv. of the hydroperoxide to give a complete reaction after five hours and product in a good yield. The epoxide of formula 4 tends to be unstable. Accordingly, it is advisable to quench the excess hydroperoxide with sodium bisulfite, wash the reaction mixture several times with saturated sodium bicarbonate solution, concentrate it at 30° C. under reduced pressure, and dried it at room temperature under high vacuum. The resulting mixture of the crude product and nonane (from the hydroperoxide solution) can then be subjected to ozonolysis in step B.

Step B

A methanolic solution containing the epoxide of formula 4 can be ozonized in the presence of sodium bicarbonate, with dry ice-acetone cooling. A Polymetrics Laboratory Ozonator Model T-816 (Polymetrics, Inc.) can be used to generate the ozonized air (shell pressure 6 PSIG; flow rate 4 LPM; 110 V). This is followed with a reduction with dimethyl sulfide to obtain the ketone of formula 5. Sodium bicarbonate should be removed by filtration prior to concentration below 30° C.

Step C

The compound of formula 5 can be oxidized under modified Baeyer-Villiger oxidation conditions (excess meta-chloroperbenzoic acid in the absence of base) in a mixture of hexane and ethyl acetate. Greater amounts of hexane in the mixture accelerate the reaction. However, a too high ratio of hexane to ethyl acetate causes an additional layer in the reaction mixture and the production of by-products. A 3:1 mixture of hexane to ethyl acetate was found particularly suitable.

Step D

The acetate of formula 6 can be hydrolyzed in methanol with a catalytic amount of sodium methoxide (15 mol %) with ice-water cooling. The product of formula 7 can then be crystallized from ethyl acetate-hexane and isolated.

Step E

Selective protection of the secondary alcohol over the tertiary alcohol in formula 7 can be achieved using known protection technology, such as t-butyldimethylsilyl chloride and imidazole in tetrahydrofuran. Other silyl protective groups, such as trimethylsilyl, triethylsilyl, tripropylsily, triisopropylsilyl, dimethylthexylsilyl, triphenylsilyl, and t-butyldiphenylsilyl protective groups can be similarly used, when a corresponding silylchloride is reacted with the compound of formula 7 in the presence of base, such as imidazole, pyridine, or other aromatic or aliphatic tertiary amine. Imidazole hydrochloride that precipitates from the reaction mixture can be removed by filtration. The filtrate can be concentrated and then introduced to the next step without further purification. Alternatively, silylation may be performed in pyridine and the reaction mixture can then be added directly to the dehydration mixture (i.e., pyridine/thionyl chloride) in Step F.

Step F

The protected (for example silyl) ether of formula 8 can be dehydrated to give the compound of formula 1A on treatment with thionyl chloride in pyridine. Adding a THF solution of the compound of formula 8 into a preformed, cold thionyl chloride/pyridine mixture minimizes formation of by-product. The product can be used in the next step without purification. Although this crude product may contain protective group (for example silyl) by-products, the protective group should be stable under these dehydration conditions.

Compounds of formula 1B and 1D are enantiomers, and can be prepared from known compounds. For example, the starting material may be (+)-Carvone [Okamura, W. H.; Aurrecoechea, J. M.; Gibbs, R. A.; Norman, A. W. *J. Org. Chem.* 1989, 54, 4072] for the preparation of 1B, and the starting material may be (−)-Carvone [Jones, Joel, Jr.; Kover, W. B. *Synth. Commun.* 1995, 25, 3907] for the praparation of 1D. Thus, compound 9 or its enantiomer may be obtained from (+)-Carvone or (−)-Carvone, respectively, by diastereoselective epoxidation according to procedures set forth in the above publications. A skilled chemist having read the present specification would know how to produce a given enantiomer by choosing the corresponding enantiomeric starting material.

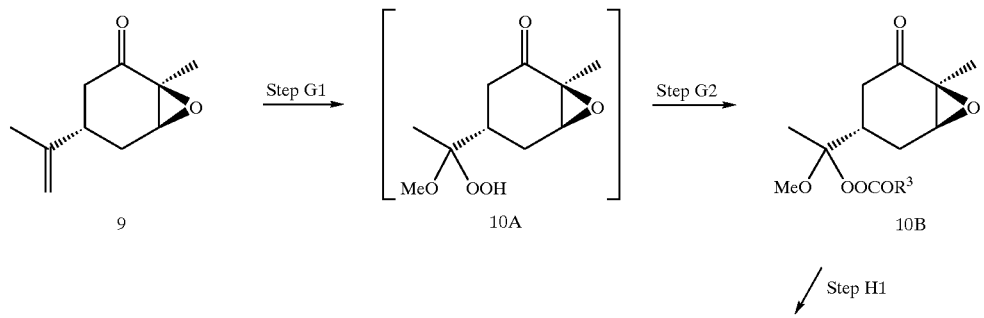

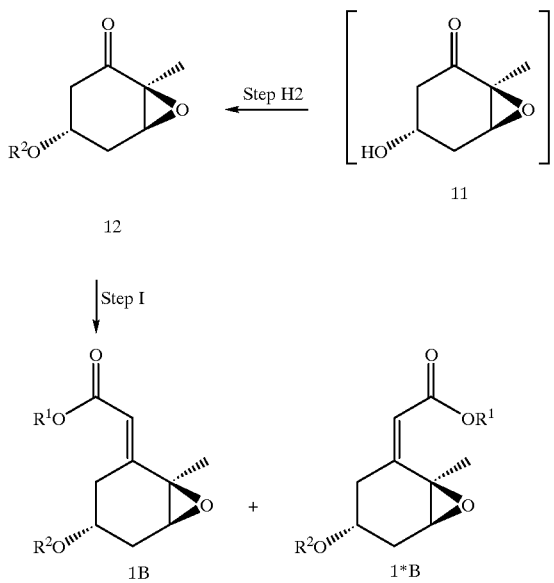

Step G

The compound of formula 9 is known [Klein, E.; Ohloff, G. Tetrahedron 1963, 19, 1091. Okamura, W. H.; Aurrecoechea, J. M.; Gibbs, R. A.; Norman, A. W. *J. Org. Chem.* 1989, 54, 40723].

At low temperature (−70° C.) a 1,3-dipolar cycloaddition of ozone to the compound of formula 9 occurs to give an ozonide, which at a higher temperature (e.g., room temperature) releases formaldehyde via a retro-1,3-dipolar cycloaddition to form carbonyl oxide. In the presence of methanol as a co-solvent, the carbonyl oxide is efficiently trapped by the alcohol to give the desired hydroperoxide of formula 10A (Step G1) which is then acylated to the compound of formula 10B (Step G2). Variations on common acylation are readily apparent to one of ordinary skill of the art. In the compound of formula 10B, $R^3$ can be $C_1$–$C_6$ alkyl, phenyl, 4-nitrophenyl, or $CF_3$. Such variations are readily made by the skilled artisan.

Excess methanol may interfere with this acylation. However, a clean reaction can be achieved with 4 equivalents of methanol. Then, the hydroperoxide can be acetylated in situ with 7 equivalents of acetic anhydride and triethylamine in the presence of a catalytic amount of DMAP at−5° C. to obtain peroxyacetate 10B, where R is a methyl group. Other acylating agents may be similarly used and the resulting peroxyester subjected to the Criegee rearrangement as described below. Such apropriate acylating agents are aliphatic and aromatic acid halides (chlorides or bromides) and acid anhydrides, such as acetylchloride, acetic anhydride, propionylchloride, benzoylchloride, 4-nitrobenzoylchloride, and trifluoroacetic anhydride. These acylating agents may react with hydroperoxide 10A in the presence of base such as triethylamine, as above, to give the corresponding peroxyesters 10B, where R is methyl, ethyl, phenyl, 4-nitrophenyl, trifluoromethyl. However, a peroxyacetate 10B where R is methyl, is preferred.

Step H1

The peroxyester of formula 10B is immediately subjected to the Criegee rearrangement to yield the alcohol of formula 11, preferably in methanol. The peroxyacetate of formula 10B tends to be unstable. Accordingly, sodium acetate may be added to prevent acid-catalyzed solvolysis of the compound of formula 10 to the corresponding dimethyl acetal and Step H1 preferably follows Step G immediately. An aqueous workup of the reaction mixture should be used to remove acidic and basic by-products in order to obtain purified compound of formula 11.

Step H2

After solvent exchange with acetonitrile, the product of formula 11 can be protected (for example, silylated) to give the ketone of formula 12. The relatively volatile protective group (for example, silyl) by-products can be removed at 45° C. under high vacuum and the crude product of formula 12 obtained.

Protection of the secondary alcohol in formula 11 can be achieved using known protection technology, for example using t-butyldimethylsilyl chloride and imidazole. Other silyl protective groups, such as trimethylsilyl, triethylsilyl, tripropylsilyl, triisopropylsilyl, dimethylthexylsilyl, triphenylsilyl, and t-butyldiphenylsilyl protective groups can be similarly used, when a corresponding silylchloride is reacted with 7 in the presence of base, such as imidazole, pyridine, or other aromatic or aliphatic tertiary amine under controlled conditions to minimize elimination of the silyloxy group.

It is noteworthy that the product of the Criegee rearrangement in methanol is the alcohol of formula 11 and that the corresponding acetate ester has never been observed in the course of the reaction. This contrasts to the typical Criegee rearrangement procedure (one-pot acetylation and rearrangement in dichloromethane: Schreiber, S. L.; Liew, W. F. *Tetrahedron Lett* 1983, 24, 2363), where an acetate is usually obtained as the major product together with a smaller amount of the corresponding alcohol. Subsequent hydrolysis of the acetate to the alcohol is problematic due to elimination of the acetoxy group.

Step I

A Wittig-Horner reaction of the compound of formula 12 can be carried out using 2.2 equiv. of tri-$R^1$ phosphonoacetate (where $R^1$ is a $C_1$–$C_6$ alkyl that can be straight-chain or branched) and 1.8 equiv. of lithium hydride in a relatively small amount of THF, at a relatively low temperature (11° C.), for a longer reaction time (20 h) to minimize elimination of the protecting (for example,-silyloxy) group. The desired compound of formula 1B is thus obtained in approximately a 7–9:1 mixture with its Z-isomer (the compound of formula 1*B).

To illustrate the inventive aspects of the subject reaction, the reaction will be discussed with reference to the reaction of a species of formula 1A (formula 1A') to form the corresponding species of formula 2A (formula 2A'). The same principles hold true with its enantiomer—compound 1C, as well as the reactions of compound 1B to form 2B, and of its enantiomer—compound 1D to form 2D.

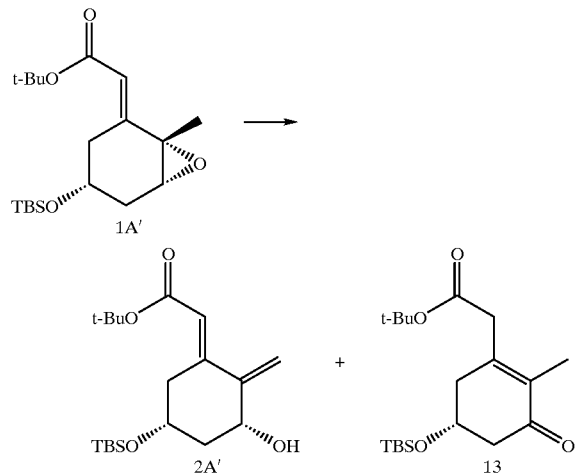

The above reaction, when using a palladium(0) triphenylphosphine catalyst [Suzuki, M.; Oda, Y.; Noyori, R. *J. Am. Chem. Soc.* 1979, 101, 1623] in THF at 65° C., results in the isomerization of epoxide 1A' to yield a mixture of the desired allyl alcohol of formula 2A' and isomeric enone of formula 13 in a ratio of 1:3 (HPLC area% at 220 nm). It has been discovered that phosphine ligands [for example, triarylphosphines, such as triphenylphosphine, tris(2-methoxyphenyl)phosphine, tris(3-methoxyphenyl) phosphine, tris(4-methoxyphenyl)phosphine, tris(o-tolyl) phosphine, tris(m-tolyl)phosphine, tris(p-tolyl)phosphine, tris(4-fluorophenyl)phosphine, tris(p-trifluoromethylphenyl)phosphine, and tris(2-furyl) phosphine, and aryl phosphines such as 1,2-bis (diphenylphosphino)ethane] in combination with palladium (0) catalyze the isomerization and that adding a fluorinated alcohol [for example 1,1,1,3,3,3-hexafluoro-2-phenyl-2-propanol and 1,3-bis(1,1,1,3,3,3,-hexafluoro-2-hydroxypropyl)benzene, perfluoro-t-butanol] increases the yield of the desired allyl alcohol of formula 2A' versus the undesired ketone of formula 13 and also improves catalyst turnover for the palladium-triphenylphosphine catalyst. The palladium-phosphine catalyst can be prepared in situ prior to the reaction from commercial palladium sources, such as Pd$_2$dba$_3$(CHCl$_3$) ("dba" stands for dibenzylideneacetone), and an excess (typically 4–5 equivalents) of the corresponding phosphine ligand, such as triphenylphosphine. Other palladium sources may be used as well, such as palladium(0) complexes Pd$_2$dba$_3$, Pddba$_2$, and palladium(II) salts Pd(OAc)$_2$, PdCl$_2$, [allylPdCl]$_2$, and Pd(acac)$_2$ ("acac" stands for acetylacetonate). Alternatively, a palladium(0)-phosphine catalyst, such as tetrakis(triphenylphosphine) palladium(0), may be separately prepared and used in the reaction. However, generation of the catalyst in situ from Pd$_2$dba$_3$(CHCl$_3$) and phosphine is preferred. With 1 mol % of the palladium-triphenylphosphine catalyst even a catalytic amount of the appropriate fluorinated alcohol was sufficient to increase the selectivity for allyl alcohol of formula 2A' to 10:1. Increasing the amount of fluorinated alcohol of formula 15c further to 50 mol % and 100 mol % gave a 16:1 and 19:1 ratio of allyl alcohol of formula 2A' to isomeric enone of formula 13, respectively.

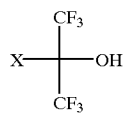

15

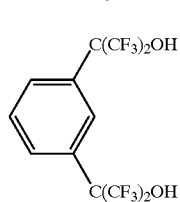

16 where X is CH$_3$ (formula 15a), H (formula 15b), phenyl (formula 15c), or CF$_3$ (formula 15d).

It has been discovered that selectivity correlated to the pK$_a$ of the fluorinated alcohols. Fluorinated alcohols with pK$_a$ <9 were particularly effective. As shown in Table 1, a sharp increase in selectivity for the desired allyl alcohol of formula 2A' occurs when the pK$_a$ of the additive dropped from 9.3 to below 8.8, suggesting a divergent reaction pathway involving protonation of an intermediate of comparable basicity. Other proton sources, such as methanol, phenols and carboxylic acids, result in no or incomplete reaction, presumably due to destruction of the catalyst.

TABLE 1 pK$_a$ of Additive vs. Selectivity.

| Alcohol Additive | Mol % | pK$_a$ in water | % (formula 2A' vs. formula 13) |
|---|---|---|---|
| t-BuOH | 100 | 19 | 25 |
| MeC(CF$_3$)$_2$OH (formula 15a) | 10 | 9.51 | 26 |
| (CF$_3$)$_2$CHOH (formula 15b) | 10 | 9.13 | 32 |
| PhC(CF$_3$)$_2$OH (formula 15c) | 10 | 8.52 | 91 |
| (CF$_3$)$_3$COH (formula 15d) | 10 | 5.18 | 95 |
| Formula 16 | 10 | 8.48 | 92 |

Although the most acidic perfluoro-tert-butanol (formula 15d) gave a better selectivity (ratio of allyl alcohol of formula 2A' to isomeric enone of formula 13=95:5) than the less acidic fluorinated alcohols of formulas 15c and 16, the reactions run with the alcohols of formulas 15c and 16 were cleaner than those with 15d. Using the fluorinated alcohol of formula 16, better results (ratio of allyl alcohol of formula 2A' to isomeric enone of formula 13>99:1) were obtained by carrying out the reaction with 1 mol % of the palladium catalyst [prepared in situ from 0.5 mol % of Pd$_2$dba$_3$(CHCl$_3$) and 5 mol % of triphenylphosphine] and 2 mol % of the alcohol of formula 16 in a less polar solvent, toluene, at the lower temperature of 35° C. This lower reaction temperature also increased the purity of the product.

The 7:1 mixture of the compound of formula 1B' (formula 1B' is the formula 1B wherein R$^1$ is t-Bu and R$^2$ is TBS) and the compound of formula 1*B' (the Z-isomer of the compound of formula 1B') was subjected to the palladium catalyzed isomerization reaction as described above to yield a 88:12 mixture of the desired allylic alcohol of formula 2B' (formula 2B' is the formula 2B wherein R$^1$ is t-Bu and R$^2$ is TBS) and its corresponding ketone (see the following Table). Thus, the regioselectivity depends on the stereochemistry of the diene oxide double bond. Isomers 1B (E-isomer) and 1*B (Z-isomer) can be separated by chromatography. From pure E-isomers 1B the desired allylic alcohols (2B' and 2B") were obtained with high selectivity (>99%). On the other hand, (Z)-diene oxides 1*B gave ketones 13 and 14 selectively (see the table below). Both ethyl and t-butyl esters gave similar results.

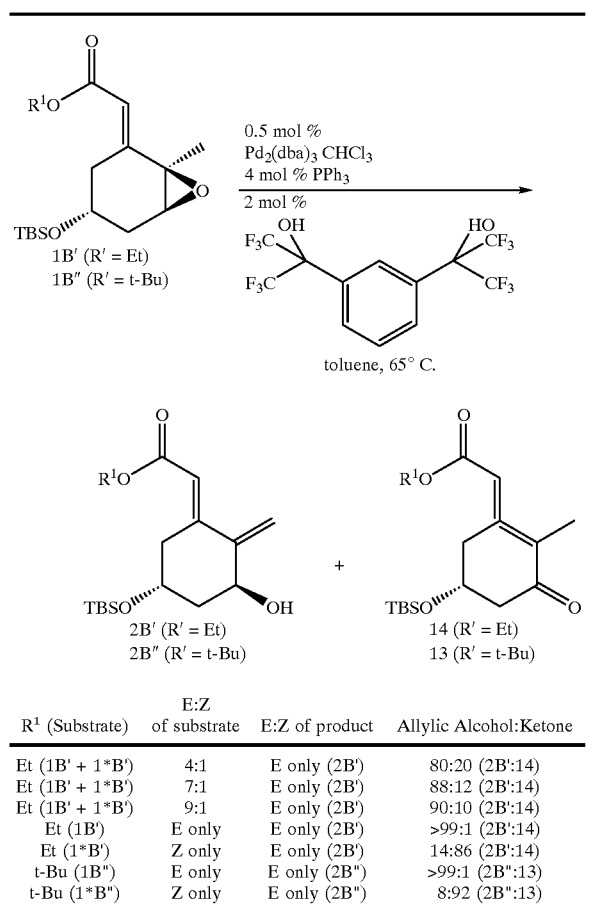

| $R^1$ (Substrate) | E:Z of substrate | E:Z of product | Allylic Alcohol:Ketone |
|---|---|---|---|
| Et (1B' + 1*B') | 4:1 | E only (2B') | 80:20 (2B':14) |
| Et (1B' + 1*B') | 7:1 | E only (2B') | 88:12 (2B':14) |
| Et (1B' + 1*B') | 9:1 | E only (2B') | 90:10 (2B':14) |
| Et (1B') | E only | E only (2B') | >99:1 (2B':14) |
| Et (1*B') | Z only | E only (2B') | 14:86 (2B':14) |
| t-Bu (1B") | E only | E only (2B") | >99:1 (2B":13) |
| t-Bu (1*B") | Z only | E only (2B") | 8:92 (2B":13) |

Although a high selectivity (>99%) was achieved with the pure E-isomers of formula 1B, under commercial conditions it may not be practical to separate the E-isomers 1B from the Z-isomers 1*B. Thus, in practice a mixture of E/Z-isomers will typically be subjected to the epoxide opening and, after solvent exchange with DMF, the resulting mixture of allylic alcohol 2B'/2B" and ketone 14/13 will be subjected to silylation. Silylation is typically achieved using t-butyldimethylsilyl chloride and imidazole using known protection technology. Other silyl protective groups, such as trimethylsilyl, triethylsilyl, tripropylsilyl, triisopropylsilyl, dimethylthexylsilyl, triphenylsilyl, and t-butyldiphenylsilyl protective groups can be similarly used, when a corresponding silylchloride is reacted with alcohol 2B. Since alcohol 2B'/2B" is converted to a non-polar product by silylation, while the polar ketone remains unchanged, pure silylated product can be easily isolated by a simple silica gel filtration.

The following examples were actually performed and are illustrative of the invention. Modifications of these examples to produce related compounds as shown in the various schemes herein are obvious chemical modifications to a person of ordinary skill in the art.

EXAMPLE 1

Preparation of the Allyl Alcohol of Formula 2A'

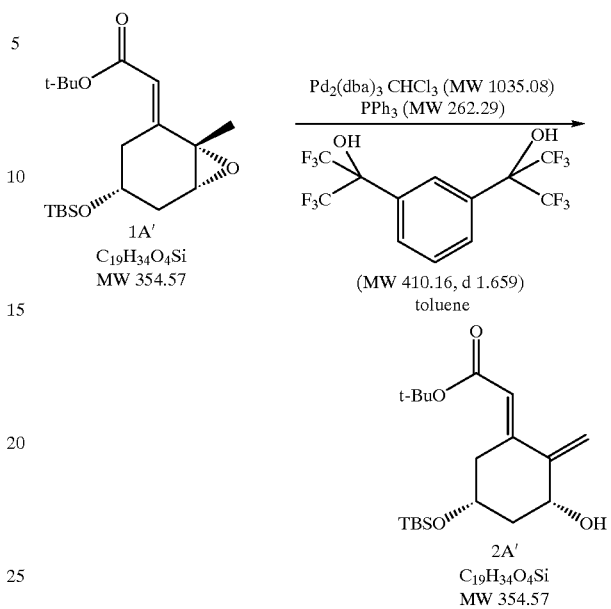

The product of this reaction may undergo a Diels-Alder dimerization as a concentrated solution and in the solid phase, at room temperature. Thus, it should be stored at −20° C.

A 500 mL, three-necked, round-bottomed flask equipped with a magnetic stirrer, septum stoppers and a thermometer was charged with 570 mg (0.551 mmol) of tris(dibenzylideneacetone) dipalladium(0)-chloroform adduct and 1.45 g (5.55 mmol) of triphenylphosphine. The flask was evacuated and refilled with nitrogen three times, then charged with 35 mL of toluene via a syringe. The resulting deep purple mixture was stirred at ambient temperature for 1 h to give a yellow slurry. Then, 0.54 mL (2.18 mmol) of 1,3-bis-(1,1,1,3,3,3-hexafluoro-2-hydroxypropyl) benzene was added. The slurry became red-orange. After three minutes of stirring at ambient temperature (19° C.), a solution of 40.7 g (110 mmol, in theory) of crude compound of formula 1A' in 160 mL of toluene, prepared in a similar manner described above for the catalyst solution (i.e., the flask containing the crude compound of formula 1A' was evacuated and refilled with nitrogen three times, then the toluene was added via a syringe), was added to the resulting catalyst solution, via a cannula using a slight positive pressure of nitrogen. After ten minutes of stirring at ambient temperature under a slight positive pressure of nitrogen, the reaction mixture was heated to 32° C. overnight (15 hours), then to 35° C. for 2 h. The reaction mixture was quickly concentrated on a rotary evaporator at 25° C. (bath temperature) under reduced pressure (oil pump) and the residue was dried under high vacuum for 30 min to give 44.8 g (overweight) of crude compound of formula 2A' as a reddish oil. This material was used immediately without further purification in subsequent reactions, as described in prior work: Shiuey, S.-J.; Kulesha, I.; Baggiolini, E. G.; Uskokovic M. R. *J. Org. Chem.* 1990, 55, 243. HPLC analysis indicated this material to be about 87% pure with about 3% of the starting material compound of formula 2A', less than 1% of the ketone by-product and about 3% of the dimer present.

In-process controls: NMR (CDCl$_3$), TLC (3:1 hexane-:ethyl acetate; short-wave UV detection and PMA stain; $R_f$ compound of formula 1A'=0.74, $R_f$ compound of formula 2A'=0.45 and $R_f$ of the ketone=0.50) and HPLC.

Reaction at 35° C. overnight is preferred as the described procedure resulted in incomplete reaction (about 3% of the starting material was observed after stirring at 32° C. for 15 h, then at 35° C. for 2 h).

The percentages given are the area percentages of the corresponding peaks at 220 nm. The HPLC conditions are as follows:

Column: Nucleosil 5 μm, 4.6×250 mm

Mobile Phase: 2% isopropanol in hexanes at 0.5 mL/min

Retention Times: 7.6 min (the compound of formula 1A'), 8.8 min (the ketone by-product), 8.9 min (dibenzylidene-acetone), 12.1 min (the compound of formula 2A') and 18 min (the dimer).

EXAMPLE 2
Preparation of Diene-Ester of Formula 3B'

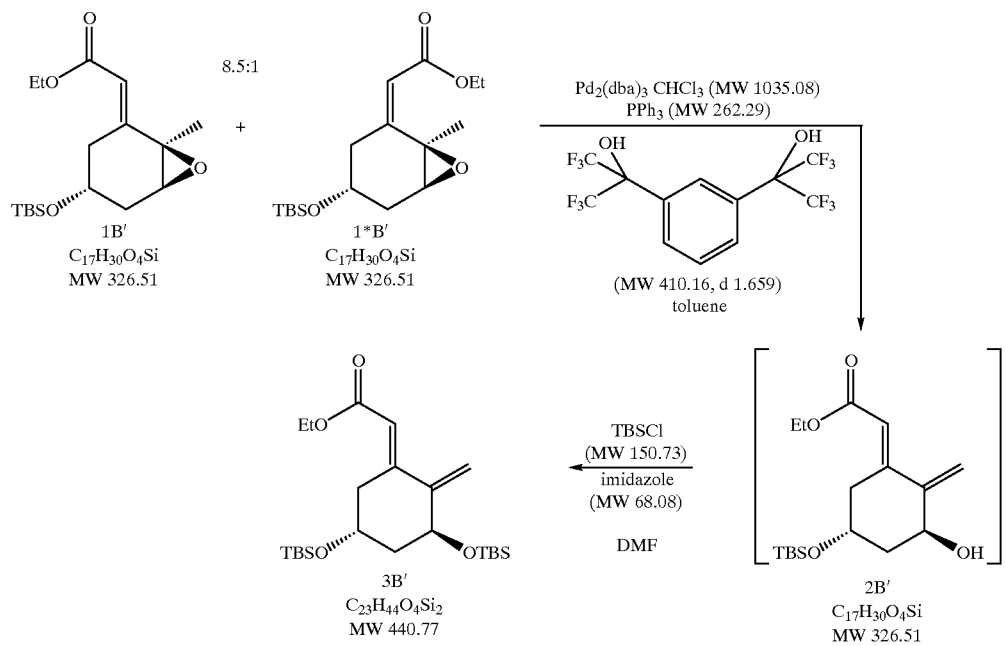

A 250 mL round-bottomed flask equipped with a magnetic stirrer, septum stopper, thermocouple and nitrogen bubbler was charged with 388 mg (0.375 mmol) of tris(dibenzylideneacetone)dipalladium(0)-chloroform adduct and 985 mg (3.75 mmol) of triphenylphosphine. The flask was evacuated and refilled with nitrogen three times, then charged via syringe with 23 mL of toluene. The resulting deep purple mixture was stirred at ambient temperature for 30 min to give a light orange suspension. Then, 370 μL (1.5 mmol) of 1,3-bis-(1,1,1,3,3,3-hexafluoro-2-hydroxypropyl)benzene was added. The mixture turned red-orange and most of the solids dissolved. After three minutes of stirring at ambient temperature (19° C.), to the resulting catalyst solution was added, via cannula using a slightly positive nitrogen pressure, a solution of 24.4 g (74.9 mmol) of crude compound of formula 1B'/1*B' (E/Z 8.5:1) in 100 mL of toluene, prepared in a similar manner to that described above for the catalyst solution (the flask containing the crude compound of formula 1B' was evacuated and refilled with nitrogen three times, then the toluene was added via cannula). After ten minutes of stirring at ambient temperature under slightly positive nitrogen pressure, the reaction mixture was heated to 40° C. overnight (16 hours). TLC analysis indicated complete reaction. The mixture was concentrated on a rotary evaporator at <40° C. under reduced pressure to remove most of the toluene. The resulting brown oil was dissolved in 80 mL of DMF and the resulting solution was cooled with an ice-water bath, then 6.12 g (89.8 mmol) of imidazole followed by 13.5 g (89.8 mmol) of t-butylchlorodimethylsilane were added. After 10 min, the cooling bath was removed and stirring was continued at room temperature overnight. TLC analysis indicated complete reaction. The reaction mixture was diluted with 300 mL of hexanes and washed with 2×150 mL=

300 mL of water. The combined aqueous washes were back-extracted with 2×100 mL=

200 mL of hexanes and the combined back-extracts were washed with 2×50 mL=

100 mL of water. All the organic layers were combined, dried over magnesium sulfate and concentrated to dryness to give a yellow, viscous oil (35.6 g, overweight). This material was dissolved in 100 mL of hexanes and the resulting solution was filtered through 200 g of TLC silica gel. The silica gel pad was then washed with 1.5 L of 98:2 hexane:ethyl acetate, and the combined filtrate and washes were concentrated to dryness under reduced pressure to give 27.7 g (84.0%) of the compound of formula 3B' as a colorless oil.

In-process controls: HPLC, NMR (CDCl$_3$) and TLC (3:1 pet.ether:diethyl ether; short-wave UV detection and PMA stain; $R_f$ 3B'=0.9, $R_f$ 1B'=0.85, $R_f$ 2B'=0.45, $R_f$ 14=0.6 and $R_f$ of dibenzylideneacetone=0.7, 19:1 hexane:ethyl acetate; short-wave UV detection and PMA stain; $R_f$ of the compound of formula 3B'=0.4 and $R_f$ of the compound of formula 2B'=0.1)

Preparatory Example 1

Preparation of the Epoxide of Formula 4'

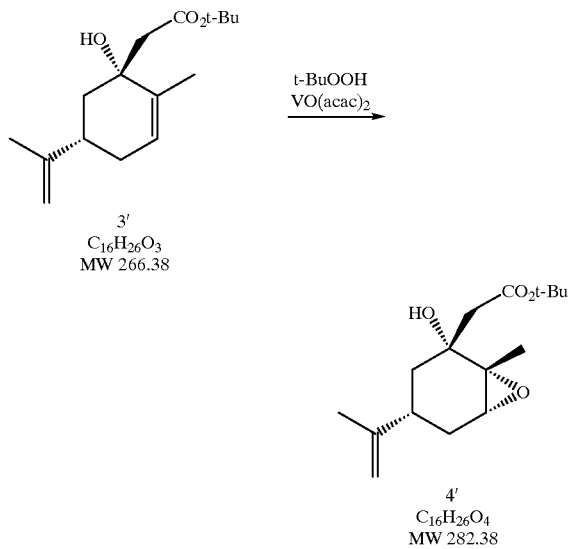

A 2 L, three-necked, round-bottomed flask equipped with a mechanical stirrer, Dean-Stark condenser, addition funnel and nitrogen bubbler was charged with
207 g (776 mmol) of the compound of formula 3',
3.09 g (11.7 mmol) of vanadyl acetylacetonate and
770 mL of cyclohexane. After the mixture was heated to gentle reflux,
170 mL (850–1020 mmol) of 5.0–6.0M tert-butyl hydroperoxide in nonane was added over 90 min. The green solution turned deep red upon addition and a mild exotherm ensued. After completion of the addition, the resulting orange-green solution was heated to reflux for 3 h. The volume of the water in the trap increased by about 4 mL. TLC analysis indicated the presence of only a small amount of starting material. After cooling to below room temperature with an ice-water bath,
77 mL of 1M sodium bisulfite solution and
150 mL of saturated sodium bicarbonate solution were added. After 5 min, an iodine-starch paper test indicated no peroxide to be present. The organic layer was separated, then washed with 3×150 mL=
450 mL of saturated sodium bicarbonate solution and
150 mL of saturated sodium chloride solution, dried over sodium sulfate, and concentrated under reduced pressure at <30° C. (bath temperature). Further drying at room temperature under high vacuum for 2 h gave 247 g (overweight) of crude compound of formula 4' containing nonane, as a pale yellow solid.

Preparatory Example 2

Preparation of the Ketone of Formula 5'

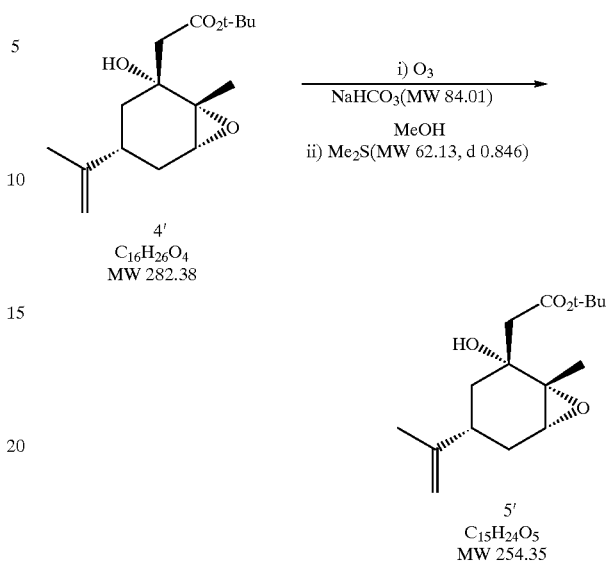

A 3 L, three-necked, round-bottomed flask equipped with a mechanical stirrer, nitrogen inlet-tube and gas outlet-tube was charged with
247 g (about 776 mmol) of the compound of formula 4',
24 g (286 mmol) of sodium bicarbonate and
1.8 L of methanol. After the mixture was cooled with a dry-ice/acetone bath, the nitrogen inlet-tube was replaced with a gas dispersion tube with porous fritted glass tip (25–50μ), and the gas outlet-tube was connected, through a trap, to a tube (4 mm I.D.) immersed in a 1M solution of potassium iodide (2 L). Then, ozonized air (4 LPM) was continuously passed through the reaction mixture at −70° C. The reaction turned pale blue after 5 h. After ozonized air was passed for an additional 15 min through the mixture at a reduced flow rate of 1 LPM, excess ozone was removed by purging with air (4 LPM) for 25 min. The resulting white suspension was treated with
75 mL (1.02 mol, about 1.3 equiv.) of methyl sulfide and allowed to warm to room temperature overnight. An iodine starch paper test indicated no peroxide to be present. The insoluble inorganic salts were removed by filtration and washed with
100 mL of ethyl acetate. The combined filtrate and washes were concentrated under reduced pressure (bath temperature ≦30° C.) to remove essentially all of the methanol. The resulting yellow, milky residue was partitioned between
1 L of ethyl acetate and
300 mL of water. The aqueous layer was separated and extracted with
50 mL of ethyl acetate. The combined organic layers were washed with
300 mL of saturated sodium chloride solution, dried over sodium sulfate, and concentrated under reduced pressure (bath temperature ≦35° C.). The resulting pale yellow oil was dissolved in
150 mL of ethyl acetate and
600 mL of hexane was added. The resulting suspension was stored in a refrigerator overnight. The solid was collected by filtration, washed with 2×200 mL=
400 mL of cold 4:1 hexane:ethyl acetate and dried by suction, then under high vacuum at room temperature to give 155.9 g (68.5% over 3 steps) of formula 5 as a white solid (mp 92–94° C.).

The combined mother liquor and washes were washed with 3×100 mL=

300 mL of saturated sodium bicarbonate solution and 100 mL of saturated sodium chloride solution, dried over sodium sulfate, and concentrated under reduced pressure (bath temperature ≦35° C.). The residue was diluted with 40 mL of ethyl acetate and 280 mL of hexane was added. The resulting slightly cloudy solution was stored in a refrigerator over the weekend. The solid was collected by filtration, washed with 4×40 mL=

160 mL of cold 7:1 hexane:ethyl acetate and dried by suction, then under high vacuum at room temperature to give 18.3 g (8.0% over 3 steps) of a second crop of the compound of formula 5' as a white solid (mp 91–93° C.).

The two crops were combined to give a total yield of 174 g (76.5% over 3 steps) of the compound of formula 5'.

In-process controls: NMR (CDCl$_3$) and TLC (1:1 hexane:ethyl acetate; PMA stain; $R_f$ the compound of formula 4'=0.70 and $R_f$ the compound of formula 5'=0.50)

Preparatory Example 3
Preparation of the Acetate of Formula 6'

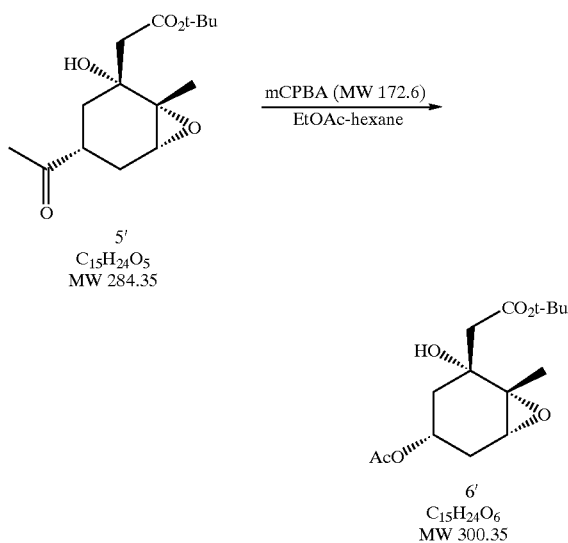

A 2 L, three-necked, round-bottomed flask equipped with a mechanical stirrer, nitrogen bubbler and thermometer was charged with 82.2 g (289 mmol) of the compound of formula 5', 115 g (606 mmol, 2.1 equiv.) of 91% m-chloroperoxybenzoic acid and 840 mL of 3:1 hexane-ethyl acetate. The white suspension was stirred at room temperature (about 20° C.) for 3 days. NMR analysis indicated about 98% conversion. After cooling to 5° C. with an ice-water bath, 145 mL (435 mmol) of 2.5M potassium carbonate solution was added dropwise at ≦12° C. over 8 min. Then, 180 mL (360 mmol) of 2M sodium sulfite solution was added over 25 min, while maintaining the temperature of the mixture below 12° C. The cold bath was removed and the mixture was stirred at ambient temperature for 90 min. NMR analysis of the organic layer indicated the presence of a 1:4 mixture of mCPBA to the product. Thus, 6 mL (82 mmol) of dimethyl sulfide was added. After the resulting thin suspension was stirred for 15 min, iodine-starch paper test indicated complete reduction. The solid was removed by filtration and washed with 100 mL of ethyl acetate. The filtrate and wash were combined and the layers were separated. The organic layer was washed with 30 mL of 10% potassium bicarbonate solution and dried over magnesium sulfate. The combined aqueous layers were extracted with 200 mL of ethyl acetate. The organic layer was washed with 20 mL of 10% potassium bicarbonate solution and dried over magnesium sulfate. The combined aqueous layers were again extracted with 200 mL of ethyl acetate. The organic layer was washed with 20 mL of 10% potassium bicarbonate solution and dried over magnesium sulfate. The combined aqueous layers were extracted one more time with 200 mL of ethyl acetate. The organic layer was washed with 20 mL of 10% potassium bicarbonate solution and dried over magnesium sulfate. All the organic layers were combined and concentrated at ≦30° C. under reduced pressure. The residue was dried under high vacuum at room temperature overnight to give 81.3 g (93.6%) of the compound of formula 6' as a colorless oil. NMR analysis indicated the presence of a small amount of ethyl acetate and a trace of the compound of formula 5'.

In-process controls: NMR (CDCl$_3$) and TLC (1:1 hexane:ethyl acetate; PMA stain; $R_f$ compound of formula 5'=0.50 and $R_f$ compound of formula 6'=0.55).

Preparatory Example 4
Preparation of Alcohol of Formula 7'

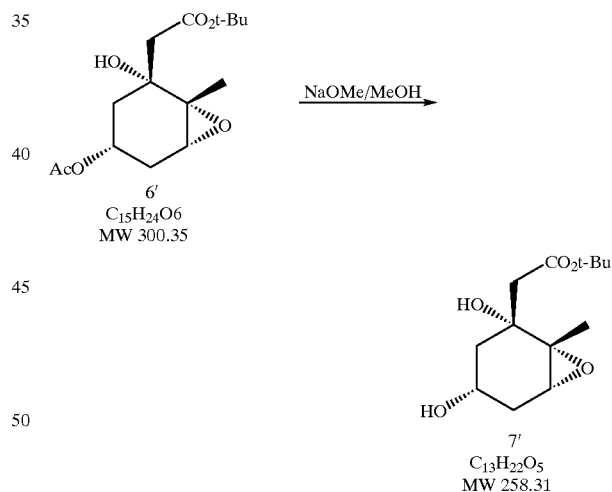

A 1 L round-bottomed flask equipped with a magnetic stirrer, nitrogen bubbler and addition funnel was charged with 81.3 g (270 mmol) of the compound of formula 6' and 270 mL of methanol. The resulting solution was stirred with ice-water cooling for 30 min and 9.3 mL (40.5 mmol, 15 mol %) of 25% sodium methoxide in methanol was added dropwise over 10 min. After stirring at 0° C. for 4 h, TLC analysis indicated complete reaction. The reaction mixture was quenched with 3.0 mL (52.6 mmol, 1.3 equiv. To sodium methoxide) of acetic acid and concentrated at ≦30° C. under reduced pressure. The resulting milky residue was dried under high vacuum at room temperature for 30 min, then partitioned between 500 mL of ethyl acetate and 50 mL of 5% potassium bicarbonate solution. The layers were separated, and the organic layer was washed with 50 mL of 5% potassium bicarbonate solution and 50 mL of saturated sodium chloride solution. The combined aqueous layers were extracted with 2×100 mL=

200 mL of ethyl acetate. The organic layers were combined, dried over magnesium sulfate and concentrated at ≦35° C. under reduced pressure. The resulting pale yellow oil (about 76 g) was dissolved in 70 mL of ethyl acetate and crystallization was induced by the addition of seed crystals. Then, 350 mL of hexane was gradually added. The resulting suspension was allowed to stand at room temperature overnight. The solid was collected by filtration, washed with 2×70 mL=

140 mL of 5:1 hexane:ethyl acetate and dried by suction, then under high vacuum at room temperature to give 54.8 g (78.4%) of the compound of formula 7' as a white solid (mp 91–92° C.). The combined mother liquor and washes were diluted with 300 mL of hexane and stored in a freezer overnight. The supernatant was removed by decantation, and the residue was dissolved in 100 mL of ethyl acetate. The solution was washed with 20 mL of 5% potassium bicarbonate solution and 20 mL of saturated sodium chloride solution, dried over magnesium sulfate and concentrated under reduced pressure (bath temperature ≦35° C.). The residue (4.3 g) was dissolved in 5 mL of ethyl acetate and, after crystallization was induced by the addition of seed crystals, 25 mL of hexane was gradually added. The resulting suspension was allowed to stand for 4 h. The solid was collected by filtration, washed with 12 mL of 5:1 hexane:ethyl acetate and dried by suction, then under high vacuum at room temperature to give 2.5 g (3.6%) of a second crop of the compound of formula 7' as an off-white solid (mp 90–92° C.). The two crops were combined to give a total yield of 57.3 g (76.7% over 2 steps) of the compound of formula 7'.

In-process controls: NMR (CDCl$_3$) and TLC (1:1 hexane:ethyl acetate; PMA stain; R$_f$ the compound of formula 6'=0.55 and R$_f$ the compound of formula 7'=0.25)

Preparatory Example 5

Preparation of the Silyl Ether of Formula 8'

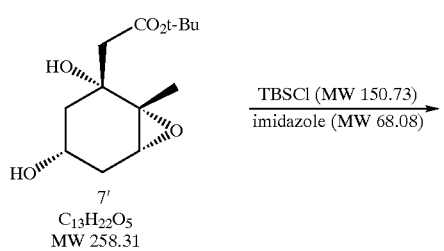

7'
C$_{13}$H$_{22}$O$_5$
MW 258.31

TBSCl (MW 150.73)
imidazole (MW 68.08)

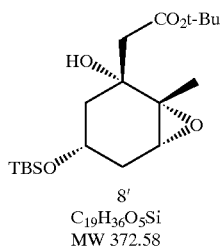

8'
C$_{19}$H$_{36}$O$_5$Si
MW 372.58

A 250 mL, three-necked, round-bottomed flask equipped with a mechanical stirrer, thermometer and nitrogen bubbler was charged with 28.6 g (111 mmol) of the compound of formula 7', 20.5 g (301 mmol) of imidazole, 19.6 g (130 mmol) of t-butylchlorodimethylsilane and 170 mL of tetrahydrofuran. An initial mild exotherm (10 to 12° C.) subsided quickly. The mixture was stirred under nitrogen overnight. TLC analysis indicated complete reaction. The solids were removed by filtration using a sintered glass funnel and washed thoroughly with 200 mL of tetrahydrofuran. The combined, colorless filtrate and wash were concentrated under reduced pressure at 25° C., then under high vacuum for 30 min to yield 48.7 g (overweight) of crude compound of formula 8' as a white solid. $^1$H NMR analysis indicated the presence of about one equivalent of protonated imidazole. This material was used directly in the next step without further purification.

In-process controls: NMR (CDCl$_3$) and TLC (1:1 hexane:ethyl acetate; PMA stain; R$_f$ the compound of formula 7'=0.16 and R$_f$ compound of formula 8'=0.79).

Preparatory Example 6

Preparation of the Unsaturated Ester of Formula 1A'

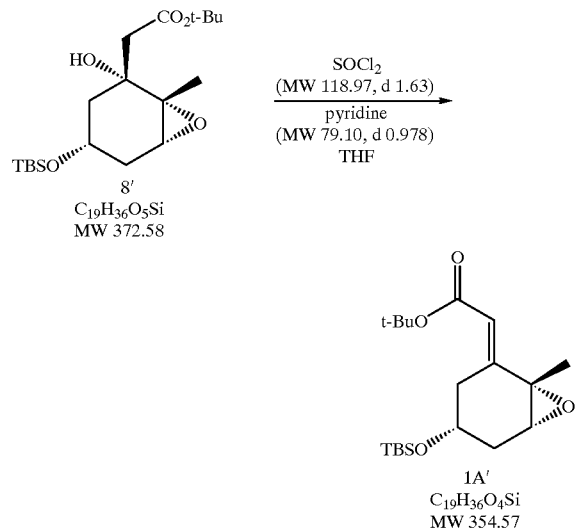

8'
C$_{19}$H$_{36}$O$_5$Si
MW 372.58

SOCl$_2$
(MW 118.97, d 1.63)
pyridine
(MW 79.10, d 0.978)
THF

1A'
C$_{19}$H$_{36}$O$_4$Si
MW 354.57

A 500 mL, three-necked, round-bottomed flask equipped with a mechanical stirrer, thermometer and nitrogen bubbler was charged with 136 mL (1.68 mol) of pyridine. Then, 13.6 mL (186 mmol) of thionyl chloride was added in one portion. The initial exotherm to 27° C. was allowed to subside and the solution was stirred at ambient temperature for 40 min. The resulting yellow solution was then cooled to −34° C. and a solution of 48.7 g (111 mmol, in theory) of crude compound of formula 8' in
86 mL of tetrahydrofuran was added dropwise over 1 h at such a rate as to maintain the temperature of the reaction at less than −25° C. The reaction mixture was allowed to warm to 0° C. over 100 min, then poured into a mixture of
700 mL of saturated sodium bicarbonate solution and
350 mL of hexanes. The resulting mixture was stirred for 30 min until there was no noticeable gas evolution occurring. The hexane layer was separated, washed with
350 mL of 1M citric acid solution, dried over sodium sulfate and concentrated to dryness under reduced pressure to yield 40.7 g (overweight) of compound of formula 1A' (about 90% pure by $^1$H NMR analysis) as a colorless oil. This material was used directly in the next step without further purification.

In-process controls: NMR (CDCl$_3$) and TLC (9:1 hexane:ethyl acetate; short-wave UV detection and PMA stain; R$_f$ the compound of formula 8'=0.04 and R$_f$ the compound of formula 1A'=0.21).

Preparatory Example 7
Preparation of the Peroxyacetate of Formula 10

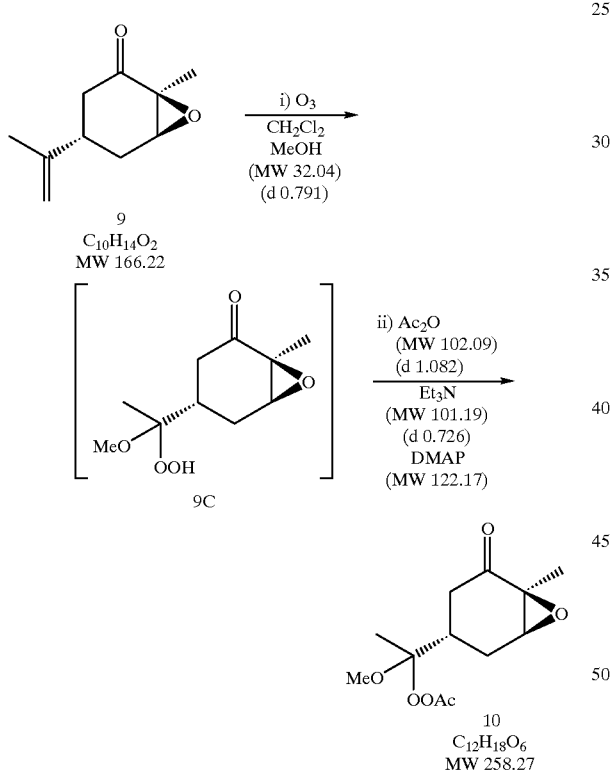

A 500 mL, three-necked, round-bottomed flask equipped with a mechanical stirrer, thermometer, nitrogen inlet-tube and gas outlet-tube was charged with
20.0 g (120 mmol) of the compound of formula 9,
20 mL (494 mmol) of methanol and
200 mL of dichloromethane. After the mixture was cooled to −68° C. with a dry-ice/acetone bath, the nitrogen inlet-tube was replaced with a gas dispersion tube with porous fritted glass tip (25–50μ), and the gas outlet-tube was connected, through a trap, to a tube (4 mm I.D.) immersed in a 1M solution of potassium iodide (2 L). Then, ozonized air (4.5 LPM) was continuously passed through the reaction mixture at −68±3° C. The reaction turned pale blue after 65 min, indicating complete reaction. Excess ozone was removed by purging with nitrogen for 30 min to give a colorless solution. The gas dispersion and outlet tubes were replaced with a nitrogen bubbler and an addition funnel. The mixture was allowed to warm to 14° C. over 40 min. After cooling to −25° C. with a dry-ice/acetone bath,
117 mL (839 mmol) of triethylamine was added over 5 min, while maintaining the temperature of the mixture below −25° C. Then,
2.0 g (16.4 mmol) of dimethylaminopyridine (DMAP) was added in one portion and
79.6 mL (843 mmol) of acetic anhydride was added slowly over 10 min, while maintaining the reaction temperature between −25° C. and −38° C. The mixture was allowed to warm to −8° C. over 30 min and stirred at −7±1° C. for 1.5 h. TLC analysis indicated complete reaction. The reaction mixture was quenched by the slow addition (over 7 min) of
33 mL of methanol, while maintaining the temperature of the mixture below 10° C. After stirring for 5 min at 5° C., the mixture was diluted with
220 mL of hexane, washed with 2×150 mL=
300 mL of 10% citric acid solution and 2×80 mL=
160 mL of saturated potassium bicarbonate solution, dried over sodium sulfate and concentrated to dryness at 35° C. under reduced pressure to give 38.2 g (overweight) of crude the compound of formula 10 as a yellow oil. This material was immediately used in the next step without further purification.

In-process controls: NMR (CDCl$_3$) and TLCs (2:1 hexane:ethyl acetate; PMA stain; R$_f$ the compound of formula 9=0.80 and R$_f$ the compound of formula 9C=0.45, 40:2:1 dichloromethane:ethyl acetate:methanol; PMA stain; R$_f$ the compound of formula 9C=0.40 and R$_f$ the compound of formula 10=0.80)

Preparatory Example 8

Preparation of the Ketone of Formula 12'

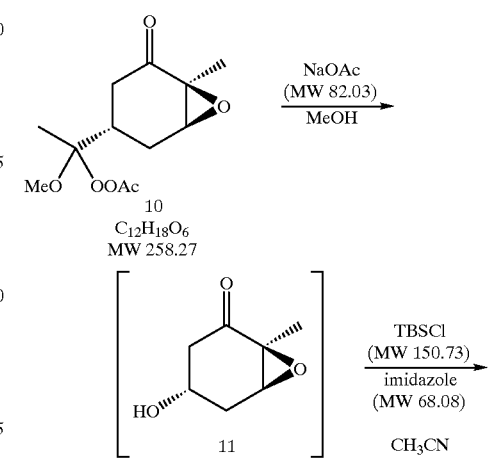

-continued

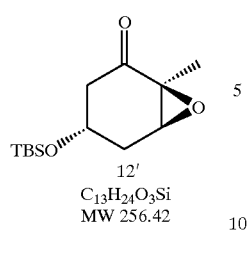

12'
C₁₃H₂₄O₃Si
MW 256.42

A 500 mL round-bottomed flask equipped with a magnetic stirrer, thermometer and nitrogen bubbler was charged with 38.2 g (120 mmol, theoretical) of crude compound of formula 10.

2 g (24.4 mmol) of sodium acetate and 245 mL of methanol. After stirring at 37° C. overnight, TLC analysis indicated complete reaction. Thus, the mixture was concentrated to dryness at 39° C. and the residue (29 g) was dissolved in 40 mL of acetonitrile. The resulting solution was concentrated to dryness at 35° C. under reduced pressure and 40 mL of acetonitrile was added. The resulting solution was again concentrated to dryness at 35° C. under reduced pressure, and 35 mL of acetonitrile and 29.5 g (433 mmol) of imidazole were added. After cooling with an ice-water bath, 32.6 g (217 mmol) of tert-butylchlorodimethylsilane was added. The cold bath was removed and the mixture was stirred at room temperature for 4 h. TLC analysis indicated the presence of only a trace amount of starting material. The reaction mixture was quenched by the addition of 10 mL of methanol. A mild exotherm ensued that raised the temperature of the mixture by 2° C. After stirring for 5 min, 55 mL of ice water was added and the mixture was extracted with 2×50 mL=

100 mL of hexane. The combined organic layers were washed with 50 mL of 2:3 methanol:water, dried over sodium sulfate and concentrated to dryness at 40° C. under reduced pressure. Further drying of the residue at 46° C. and 0.4 mmHg for 1 h gave 25.2 g of crude compound of formula 12' as a pale yellow oil. This material was used directly in the next step without further purification.

In-process controls: NMR (CDCl₃) and TLCs (40:2:1 dichloromethane:ethyl acetate:methanol; PMA stain; $R_f$ the compound of formula 10=0.8, $R_f$ the compound of formula 11=0.4 and $R_f$ compound of formula 12'=0.95, 8:1 hexane:ethyl acetate; PMA stain; $R_f$ the compound of formula 12'=0.6 and $R_f$ of tert-butyldimethylsilanol=0.5)

Preparatory Example 9
Preparation of the Unsaturated Ester of Formula 1B'

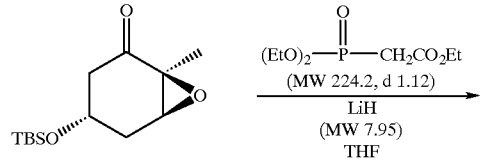

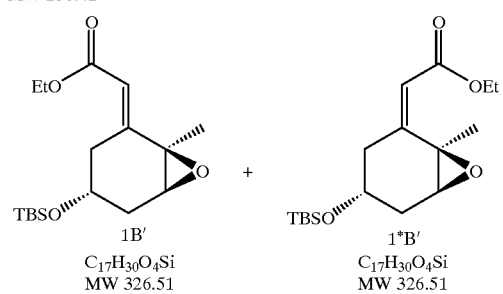

A 250 mL, three-necked, round-bottomed flask equipped with a magnetic stirrer, condenser, thermometer and nitrogen bubbler was charged with 1.41 g (177 mmol) of lithium hydride, 43.3 mL (216 mmol) of triethyl phosphonoacetate and 45 mL of THF. The mixture was slowly heated to 55° C. and the heating bath was removed. An exotherm ensued that raised the temperature of the mixture to 69° C. over 5 min. The temperature of the mixture slowly came down to 66° C. over 55 min and a clear solution resulted. Approximately 25 mL of the THF was then removed by distillation at 50–55° C. under a slightly reduced pressure. After cooling the resulting mixture to 3° C. with an ice water bath, 25.2 g (98.4 mmol) of crude the compound of formula 12' was added in one portion. The funnel was rinsed with 15 mL of THF and the rinse was added to the reaction mixture. The mixture was stirred at 5–6° C. for 90 min, at 11° C. for 18 h, then at 24° C. for 2 h. TLC analysis indicated complete reaction. Thus, the mixture was diluted with 100 mL of 8:1 hexane:ethyl acetate, washed with 3×36 mL=

108 mL of water and concentrated to dryness at 38° C. under reduced pressure. The residue was dissolved in 115 mL of hexane and filtered through 50 g of TLC silica gel. The silica gel pad was then washed with 191 mL of 8:1 hexane:ethyl acetate, and the combined filtrate and washes were concentrated to dryness at 37° C. under reduced pressure. The residue was further dried under high vacuum for 1 h to give 24.4 g (76.1%) of crude compound of formula 1B' as a yellow oil. ¹H NMR analysis indicated this material to be a 8.5:1 mixture of the compound of formula 1B' and its corresponding Z-isomer, the compound of formula 1*B'. This material was used directly in the next step without further purification.

In-process controls: NMR (CDCl₃) and TLC (3:1 dichloromethane:hexane; short-wave UV detection and PMA stain; $R_f$ the compound of formula 12'=0.55, $R_f$ the compound of formula 1B'=0.45 and $R_f$ of the Z-isomer (compound of formula 1*B'=0.35)

Upon reading the present specification, various alternative embodiments will become obvious to the skilled artisan. These variations are to be considered within the scope and spirit of the subject invention that is only to be limited by the claims that follow and their equivalents.

What is claimed is:

1. A compound having the structure:

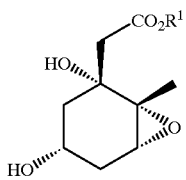

7 wherein $R^1$ is $C_1$–$C_6$ alkyl; or its enantiomer.

2. The compound of claim 1 having the structure:

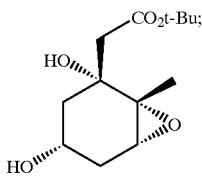

7' or its enantiomer.

3. A compound having the structure:

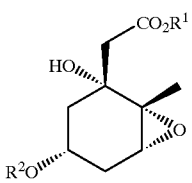

8 wherein $R^1$ is $C_1$–$C_6$ alkyl and $R^2$ is a hydroxy protective group selected from the group consisting of trimethylsilyl, triethylsilyl, tripropylsilyl, triisopropylsilyl, t-butyldimethylsilyl, dimethylthexylsilyl, triphenylsilyl, and t-butyldiphenylsilyl; or its enantiomer.

4. A compound according to claim 3 having the structure:

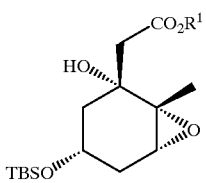

8'' wherein $R^1$ is $C_1$–$C_6$ alkyl; or its enantiomer.

5. A compound according to claim 3 having the structure:

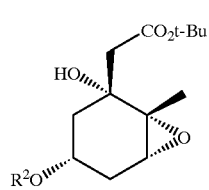

8''' wherein $R^2$ is a hydroxy protective group selected from the group consisting of trimethylsilyl, triethylsilyl, tripropylsilyl, triisopropylsilyl, t-butyldimethylsilyl, dimethyithexylsilyl, triphenylsilyl, and t-butyldiphenylsilyl; or its enantiomer.

6. The compound according to claim 5 having the structure:

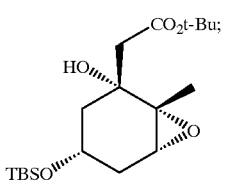

8' or its enantiomer.

7. A compound having the structure:

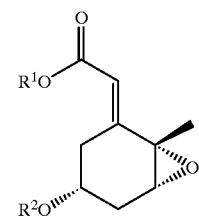

1A wherein $R^1$ is $C_1$–$C_6$ alkyl and $R^2$ is a hydroxy protective group selected from the group consisting of trimethylsilyl, triethylsilyl, tripropylsilyl, triisopropylsilyl, t-butyldimethylsilyl, dimethylthexylsilyl, triphenylsilyl, and t-butyldiphenylsilyl; or its enantiomer.

8. A compound according to claim 7 having the structure:

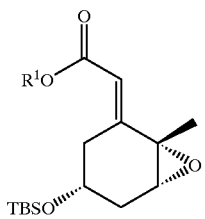

1A'' wherein $R^1$ is $C_1$–$C_6$ alkyl; or its enantiomer.

9. A compound according to claim 7 having the structure:

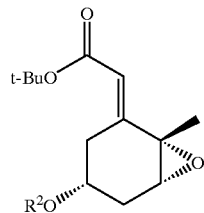

1A''' wherein R² is a hydroxy protective group selected from the group consisting of trimethylsilyl, triethylsilyl, tripropylsilyl, triisopropylsilyl, t-butyldimethylsilyl, dimethylthexylsilyl, triphenylsilyl, and t-butyldiphenylsily; or its enantiomer.

10. The compound according to claim 8 having the structure:

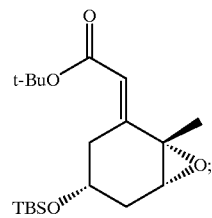

1A' or its enantiomer.

11. A compound having the structure:

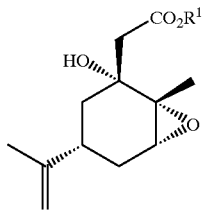

4 wherein R¹ is $C_1$–$C_6$ alkyl; or its enantiomer.

12. The compound according to claim 11 having the structure:

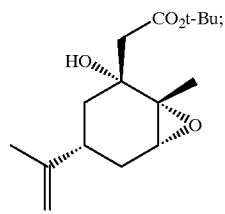

4' or its enantiomer.

13. A compound having the structure:

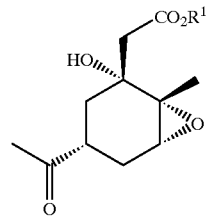

5 wherein R¹ is $C_1$–$C_6$ alkyl; or its enantiomer.

14. The compound according to claim 13 having the structure:

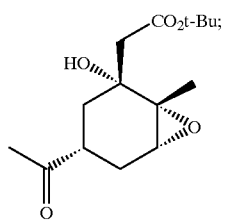

5' or its enantiomer.

15. A compound having the structure:

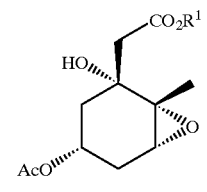

6 wherein R¹ is $C_1$–$C_6$ alkyl; or its enantiomer.

16. The compound according to claim 15 having the structure:

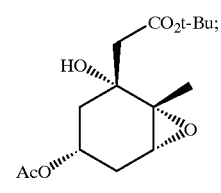

6' or its enantiomer.

* * * * *